US 8,541,031 B2
Sep. 24, 2013

(12) United States Patent
Mount et al.

(10) Patent No.: US 8,541,031 B2
(45) Date of Patent: Sep. 24, 2013

(54) DEPOSITION OF NANOCRYSTALLINE CALCITE ON SURFACES BY A TISSUE AND CELLULAR BIOMINERALIZATION

(76) Inventors: Andrew S. Mount, Mountain Rest, SC (US); Neeraj V. Gohad, Clemson, SC (US); Douglas C. Hansen, Dayton, OH (US); Karolyn Mueller, Dayton, OH (US); Mary Beth Johnstone, Clemson, SC (US)

( * ) Notice: Subject to any disclaimer, the term of this patent is extended or adjusted under 35 U.S.C. 154(b) by 559 days.

(21) Appl. No.: 12/631,526

(22) Filed: Dec. 4, 2009

(65) Prior Publication Data
US 2010/0150982 A1 Jun. 17, 2010

Related U.S. Application Data

(60) Provisional application No. 61/201,013, filed on Dec. 4, 2008.

(51) Int. Cl.
*A61K 35/56* (2006.01)
*A01N 59/06* (2006.01)

(52) U.S. Cl.
USPC ........... 424/547; 424/520; 424/682; 424/687; 435/325

(58) Field of Classification Search
USPC .......................... 424/400, 520, 547, 682, 687
See application file for complete search history.

(56) References Cited

U.S. PATENT DOCUMENTS 4,954,340 A * 9/1990 Maeda et al. .............. 424/278.1
2007/0193526 A1 * 8/2007 Batzer ........................... 119/244

* cited by examiner

*Primary Examiner* — Ruth Davis
(74) *Attorney, Agent, or Firm* — Dority & Manning PA

(57) ABSTRACT

Disclosed are articles comprising layered nanocrystalline calcite and methods for forming nanocrystalline calcite layers and compositions comprising nanocrystalline calcite layers.

21 Claims, 29 Drawing Sheets

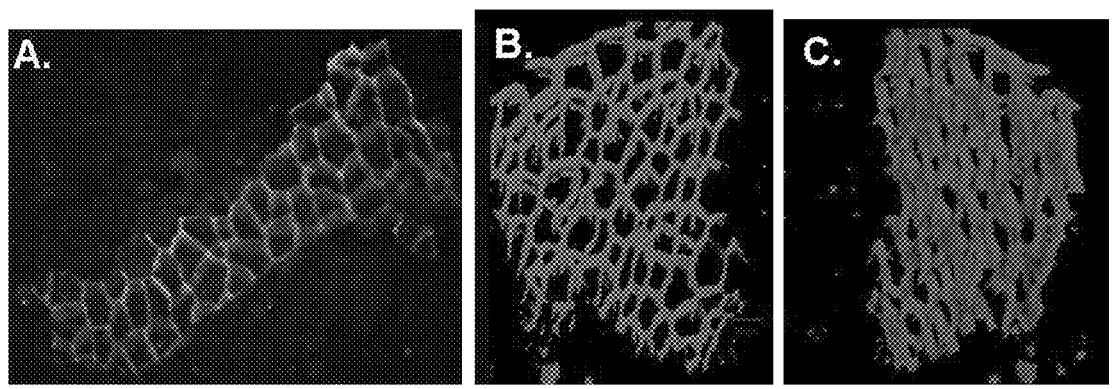
Fig. 4 A to C

US 8,541,031 B2

DEPOSITION OF NANOCRYSTALLINE CALCITE ON SURFACES BY A TISSUE AND CELLULAR BIOMINERALIZATION

PRIORITY

This application claims the benefit of Provisional Application Ser. No. 61/201,013 filed on Dec. 4, 2008, the entire disclosure of which is incorporated herein by reference.

This invention was made with government support under contract number FA9550-06-1-0133 PI issued by the Department of the Navy: Douglas Hansen, University of Dayton Research Institute; CO-PI: Andrew S. Mount, Clemson University, UDRI subcontract #2005367. The government has certain rights in the invention.

FIELD OF THE DISCLOSURE

Disclosed are articles comprising layered nanocrystalline calcite and methods for forming nanocrystalline calcite layers and compositions comprising nanocrystalline calcite layers.

BACKGROUND OF THE DISCLOSURE

The phylum Mollusca is perhaps unmatched in its ability to produce, via biological nano-engineering, rigid and light weight shell microstructures that are also visually elegant and structurally complex. The resistance to fracture forces and the over-all toughness make these materials ideal models upon which to devise novel advanced bio-ceramics. Shell formation in the Eastern oyster *Crassostrea viginica*, is a cell-driven nanoscale process that involves hemocytes (blood cells) and the outer mantle epithelial cells (OME) of the mantle organ. The resultant bio-nanocomposite is composed of crystals embedded in a pericellular micromolecular complex (PMC) comprising proteins, peptides, lipids and carbohydrates.

A light weight durable coating comprised of microcrystalline calcite would serve as a biocompatible interface between inorganic materials, inter alia, metals such as those used in medical devices, and the body. In addition, controllable formation of microcrystalline calcite would lead to the formation of macrocrystalline particles, one example of which is the synthetic pearl.

SUMMARY

The disclosed processes relate to the formation of biocompatible layers on inert surfaces. The biocompatible layers can be formed by contacting the inert surface with cells which can form either microcrystalline calcite or aragonite layers. The contacting can be accomplished in vivo or ex vivo. Further, the disclosed processes can be used to form synthetic pearls wherein the mineralized phase and the matrix phase of the formed layers have the same uniform thickness thereby providing a pearl comprising a natural as opposed to an artificial layering.

BRIEF DESCRIPTION OF THE DRAWINGS

FIG. 1A depicts prismatic shell deposits on foil implants placed distally into notched regions on the shell margin. The mineral was identified as prismatic microstructure by epi-polarized—fluorescent microscopy and SEM. Left bottom inset depicts FITC channel image of prismatic layer shows auto-fluorescent prism walls. Right bottom inset depicts the same field of view in the top inset viewed with epi-polarized light shows birefringent calcite prisms.

FIG. 1B depicts an SEM of prisms covered with an unmineralized organic membrane.

FIG. 1C depicts an SEM of an aluminum alloy (AL7075) implant that was placed near with the adductor mantle region is fully coated with multiple layers of folia.

FIG. 1D shows that folia occur on the surface of un-mineralized membrane (black arrow) and are capped with another membrane (white arrow). A yellow arrow indicates folia on the outer surface of the reflected membrane. Figure below represents the image of the boxed region show fully formed folia that are identical that of natural shell.

FIG. 1E depicts that a web-like membrane occurs between folia lath deposits (arrow).

FIG. 1F depicts the web surrounding the nanometer size crystals of nascent folia laths. The circled region shows an individual nanocrystal which has grown vertically through this web. The web membrane is a composite having a distinct fibrous core surrounded by globules along its periphery.

FIG. 1G depicts a web-like membrane that is occluded within a developing folia lath (circled) depicted in the enlargement below.

FIG. 2A depicts the SEM at low magnification (5K) of the surface of titanium (Ti6Al4V) implant showing developing folia ("pre-folia") after 8 days of implantation. Numerous pre-folia "patches" (white arrow) are evident on top of an un-mineralized membrane (black arrow).

FIG. 2B depicts membrane bound nanoparticles measuring approximately 500 nm edge length (white arrow) aggregate on the membrane surface (black arrow) forming larger particles. The membrane is granular with embedded nanoparticles of approximately 100 nm in size.

FIG. 2C depicts several vesicles that contain crystals, one (inside circle) is magnified in the insert below. Two vesicles appear fused through their plasma membranes (yellow arrow).

FIG. 2E depicts an EDS of the crystal identified in a larger micron sized vesicle (FIG. 2D) thereby confirming the presence of calcium carbonate.

FIG. 3A depicts a growth front of newly forming folia as indicated by the circle.

FIG. 3B depicts pancakes at the growth front indicated in FIG. 3A that are converging. FIG. 3C depicts a magnification of the black rectangle inset and shows the surface is highly granular and not yet organized into discernable folia. Dendritic cellular membrane and processes are visible (white arrows) and is evidence of hemocyte activity.

FIG. 3D depicts a pancake from a different region on the implant that is more developed on its surface.

FIGS. 4A to 4E depict that the membranes surrounding the periphery of individual prisms are produced by outer mantle epithelial cells and are infiltrated by hemocytes.

FIG. 4A is an Epi-fluorescent micrograph of living mantle epithelial tissue showing an intact piece of prismatic shell on tissue's surface. The periphery of each prism is surrounded by an autofluorescent organic matrix "wall" which is visible in the FITC channel. There is a 1:1 correspondence of individual prisms to each of the underlying mantle epithelial cells.

FIG. 4B is an LSM (Zeiss LSM 510) projection of the auto fluorescent prism walls as described above.

FIG. 4C is the same LSM projection but rotated to reveal the relationship of the organic membrane to the apical surface of the epithelia. There are point-like processes that are in contact with the junctional boundaries between the cells. The membrane appears to emanate from these cellular junctions.

FIG. 4D depicts the SEM micrograph of the same region of mantle epithelium. The prismatic wall membrane and the micro-ridge pattern on the apical surface of the individual cells that form the epithelia can be seen.

FIG. 4E depicts an LSM projection showing the presence of living hemocytes (calcein stained and pseudo-colored light blue) on the outer surface of prism membrane walls (green).

DETAILED DESCRIPTION

Figure 1A:
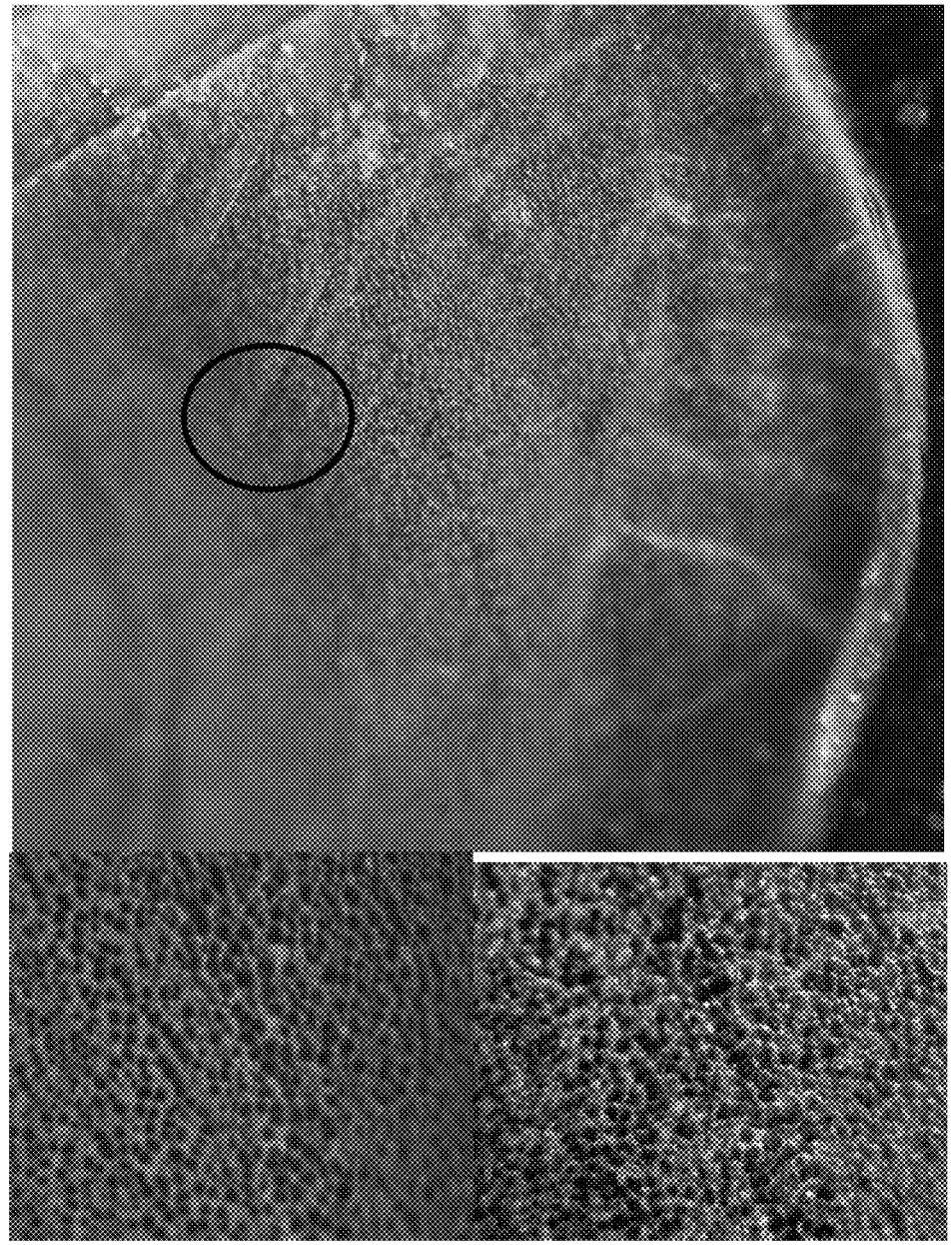
FIG. 1A to 1G relate to folia and prismatic layer formation that occurs in association with membranes on all tested metal implants. These processes can be observed independently.
Figure 1B:
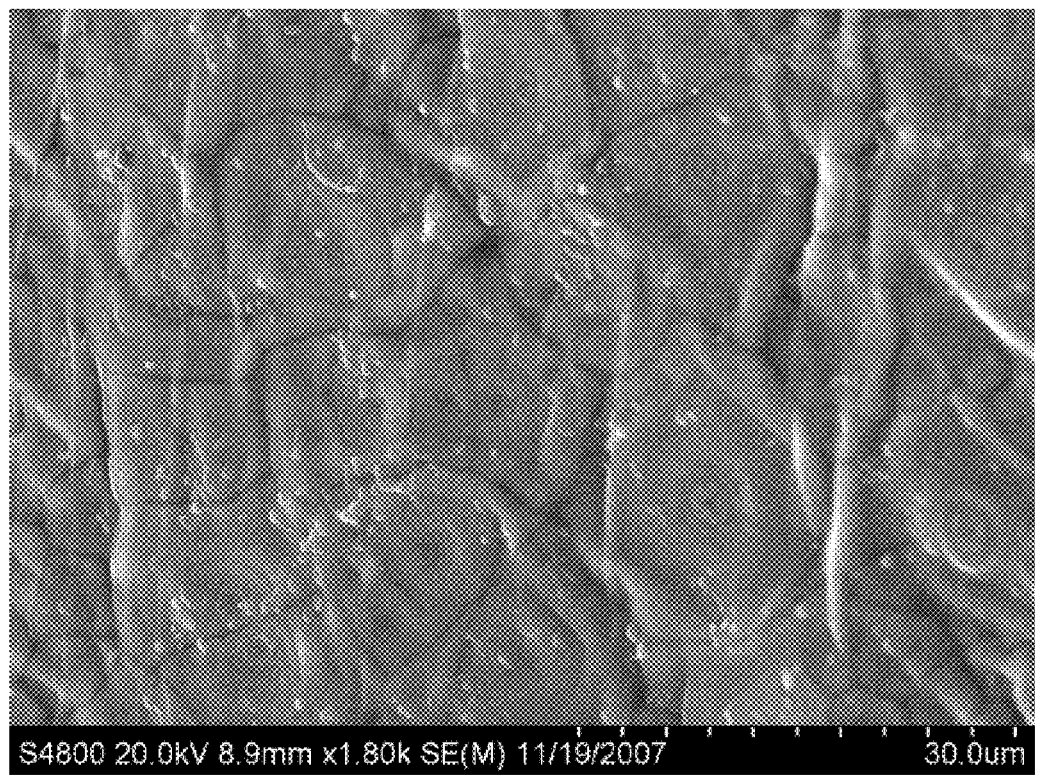
Figure 1C:
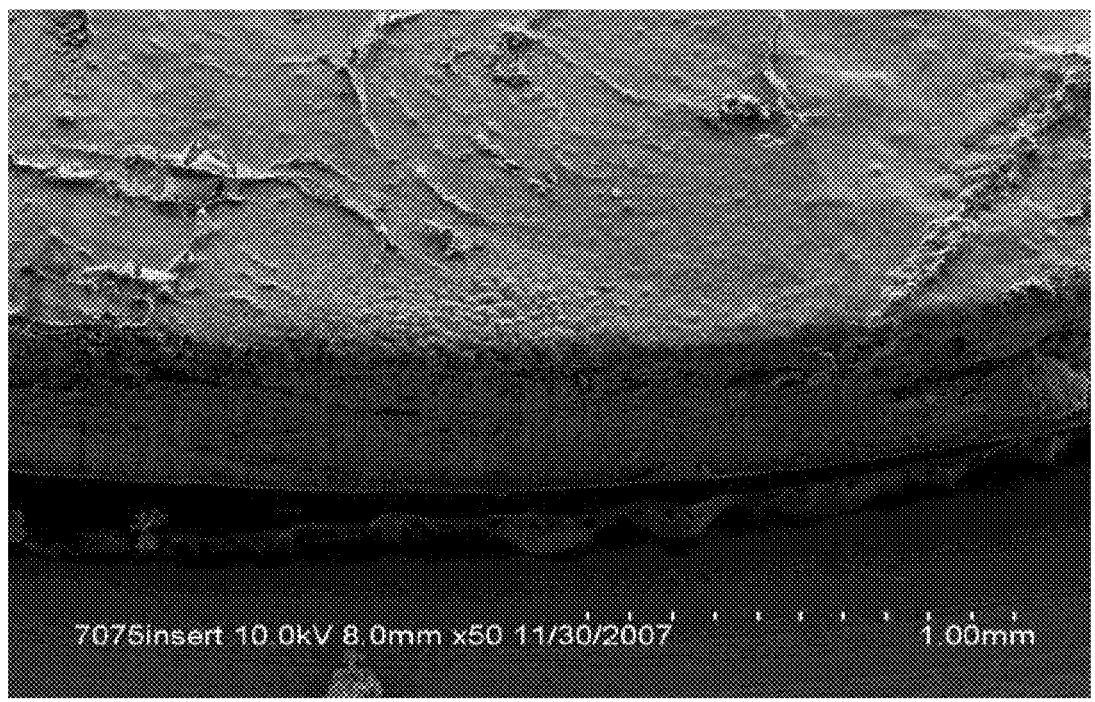
Figure 1D:
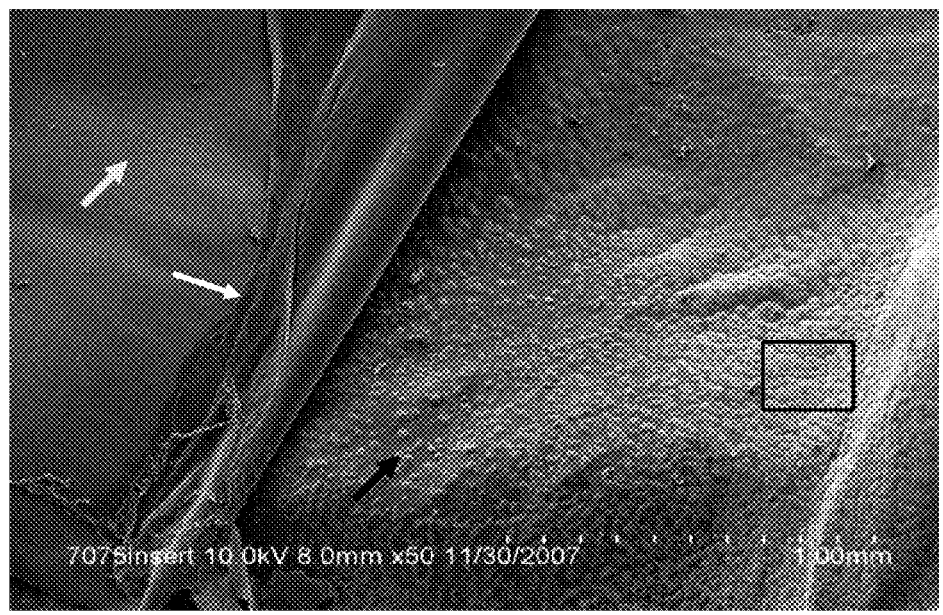
Figure 1D:
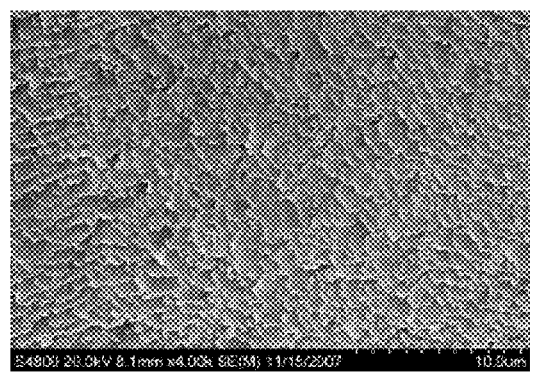
Figure 1E:
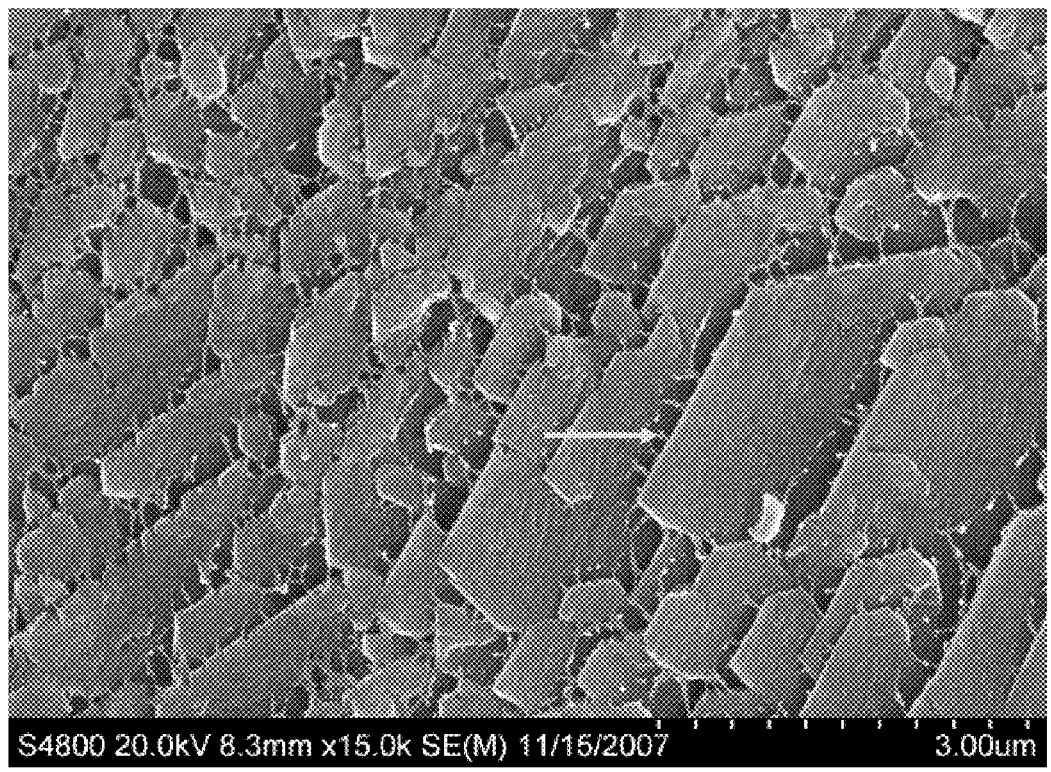
Figure 1F:
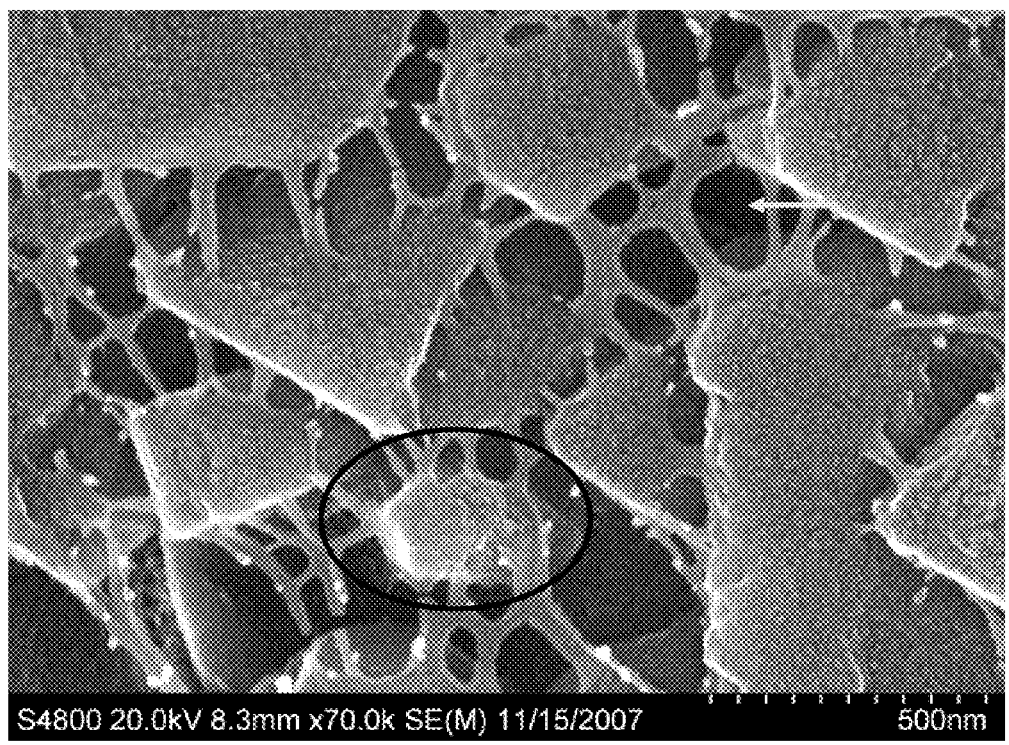
Figure 1G:
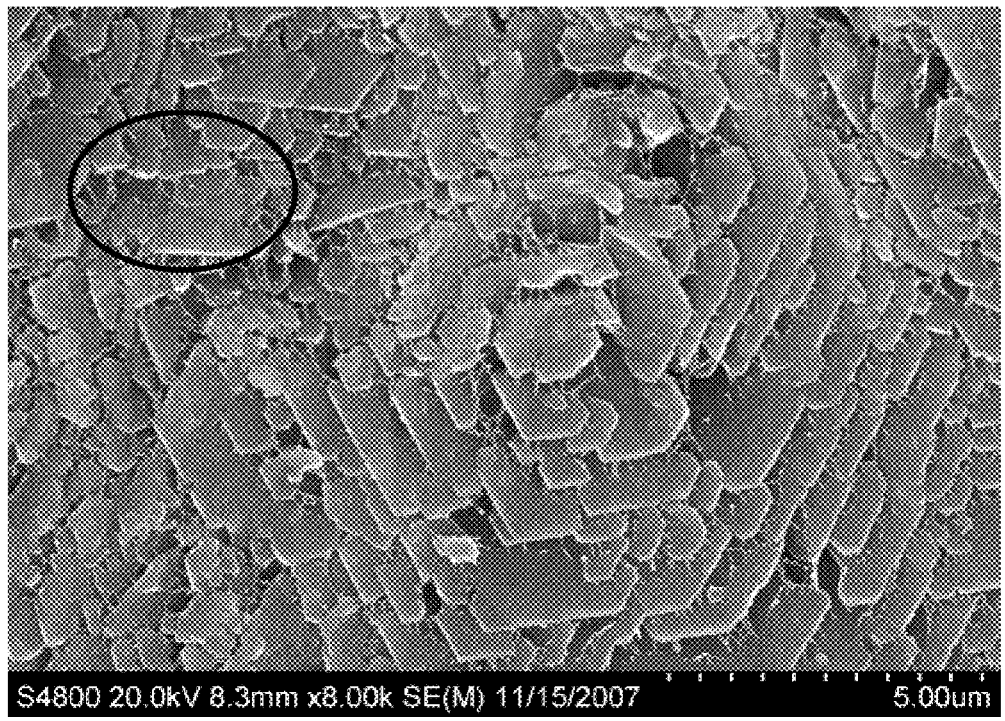
Figure 1G:
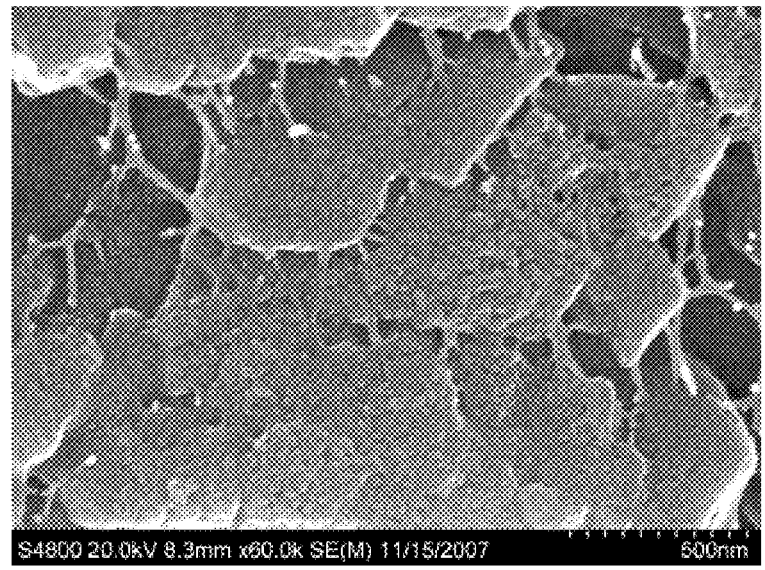
Figure 2A:
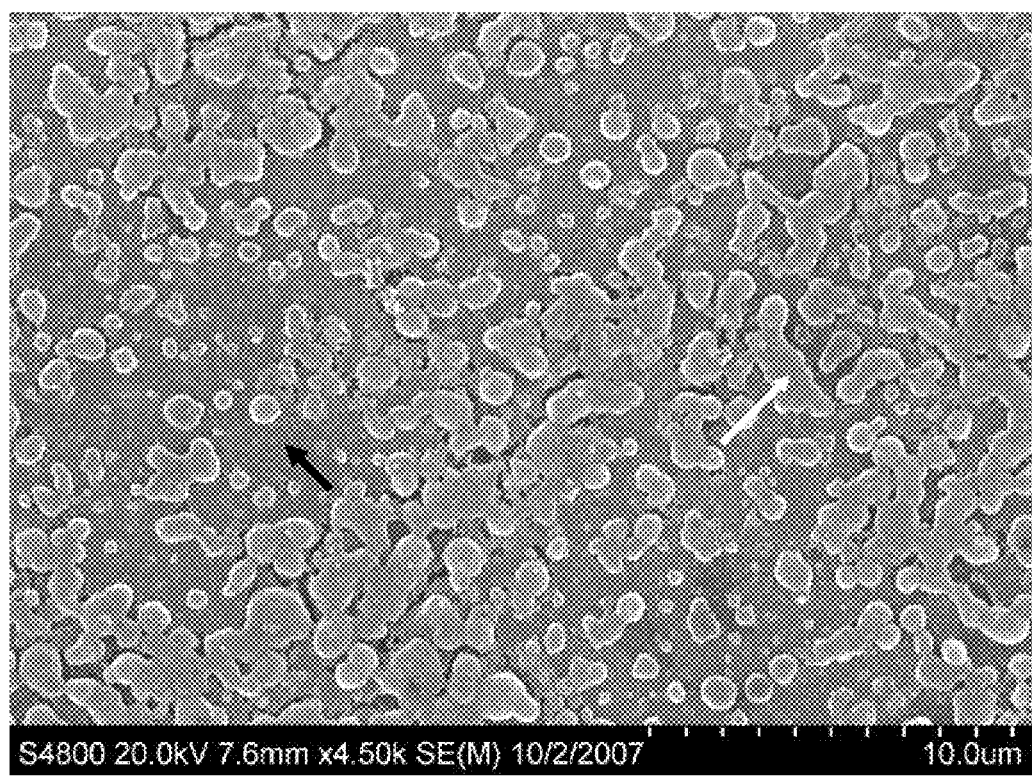
FIGS. 2A to 2E relate to cell derived exosome-like particles that initiate folia development on membranes which have covered the surface of the metal implants.
Figure 2B:
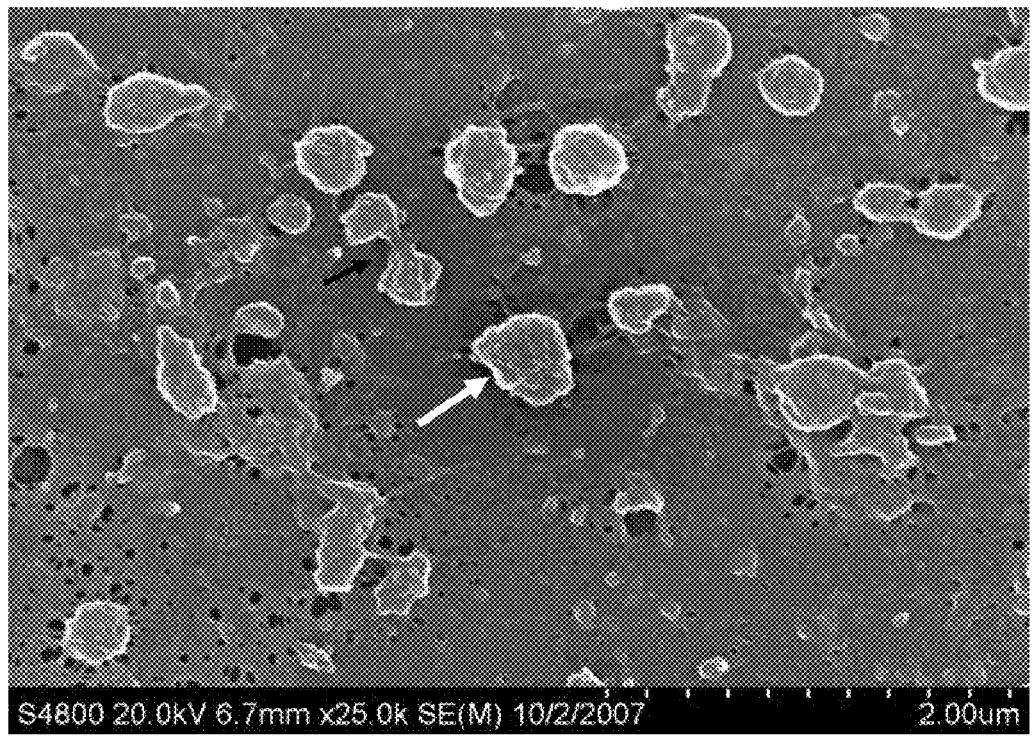
Figure 2C:
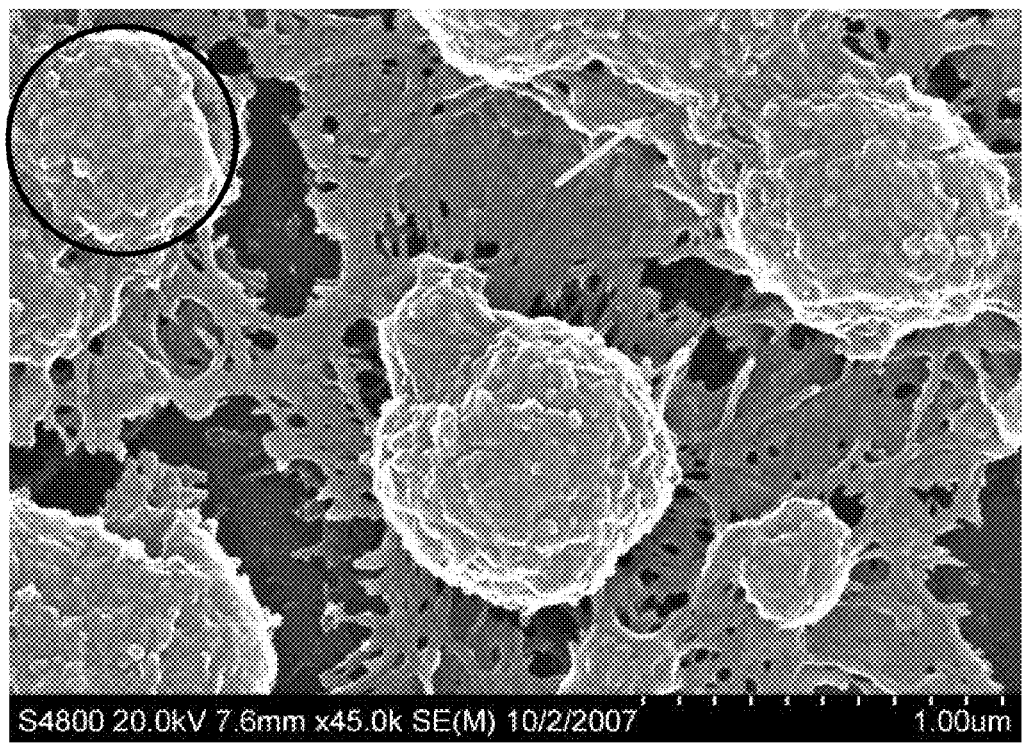
Figure 2C:
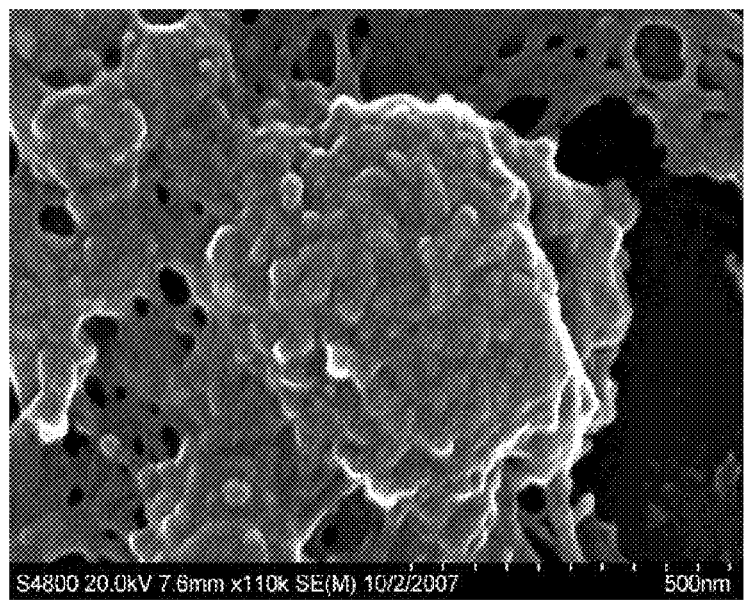
Figure 2D:
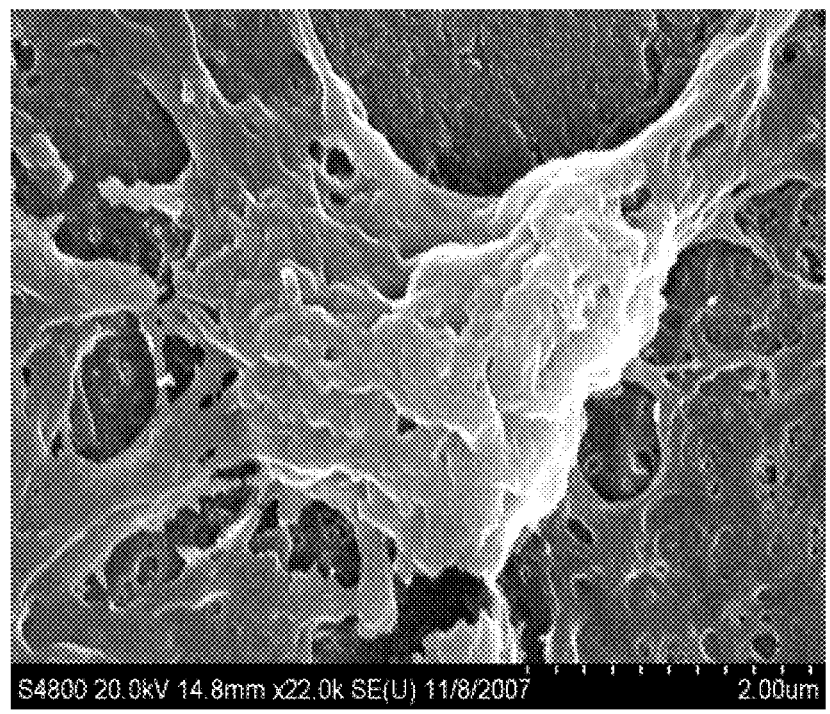
Figure 2E:
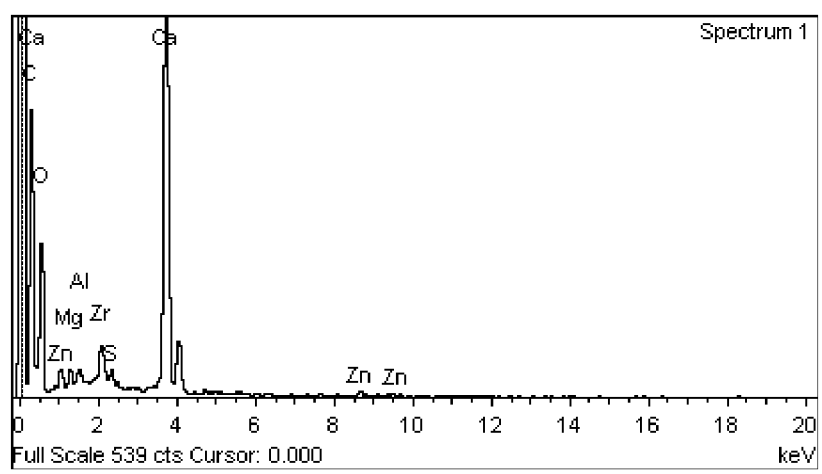
Figure 3A:
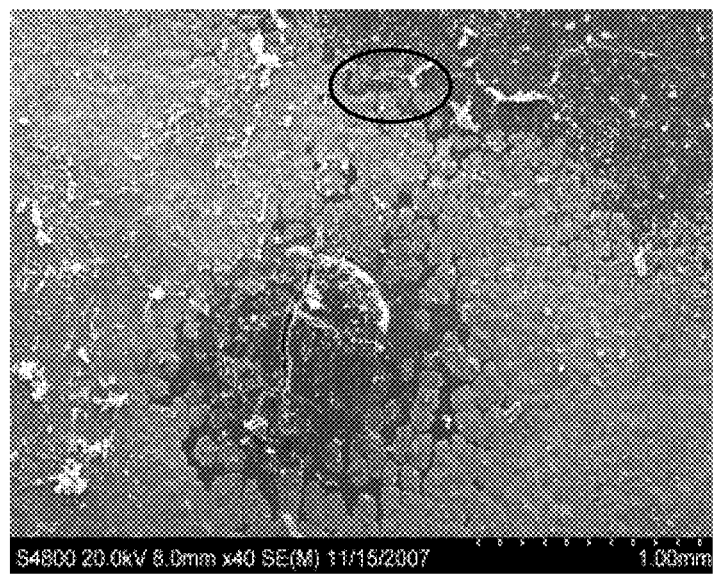
FIGS. 3A to 3D relate to hemocyte activity that is evident on developing folia surfaces wherein folia "pancakes" form on the membrane surface.
Figure 3B:
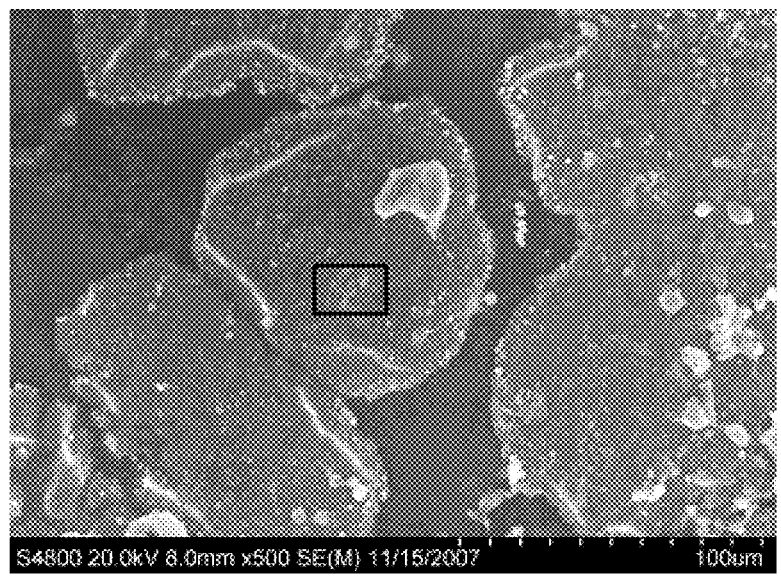
Figure 3C:
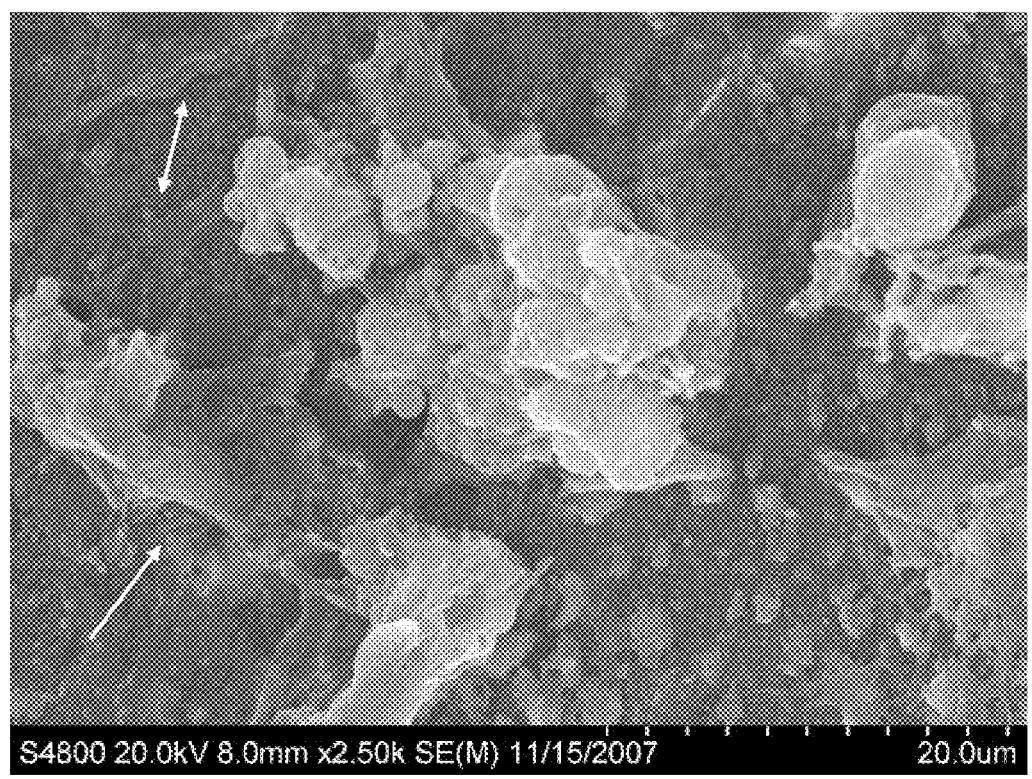
Figure 3D:
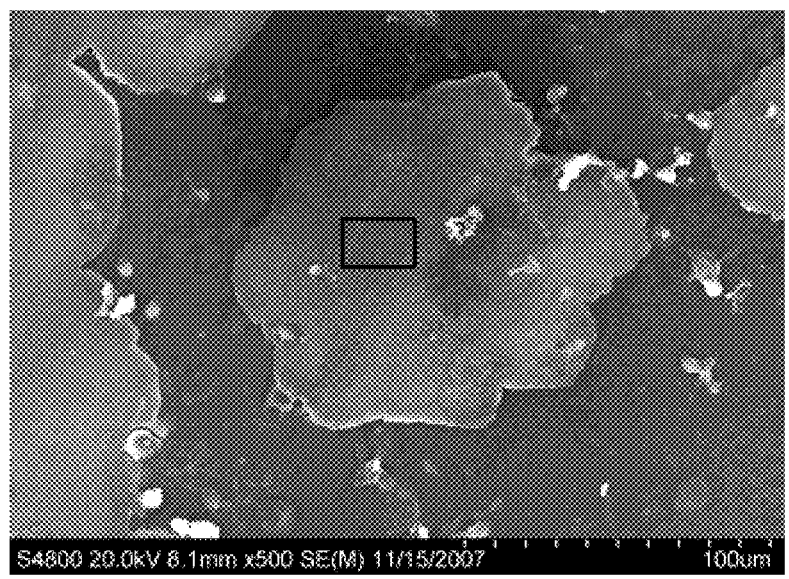
Figure 3E:
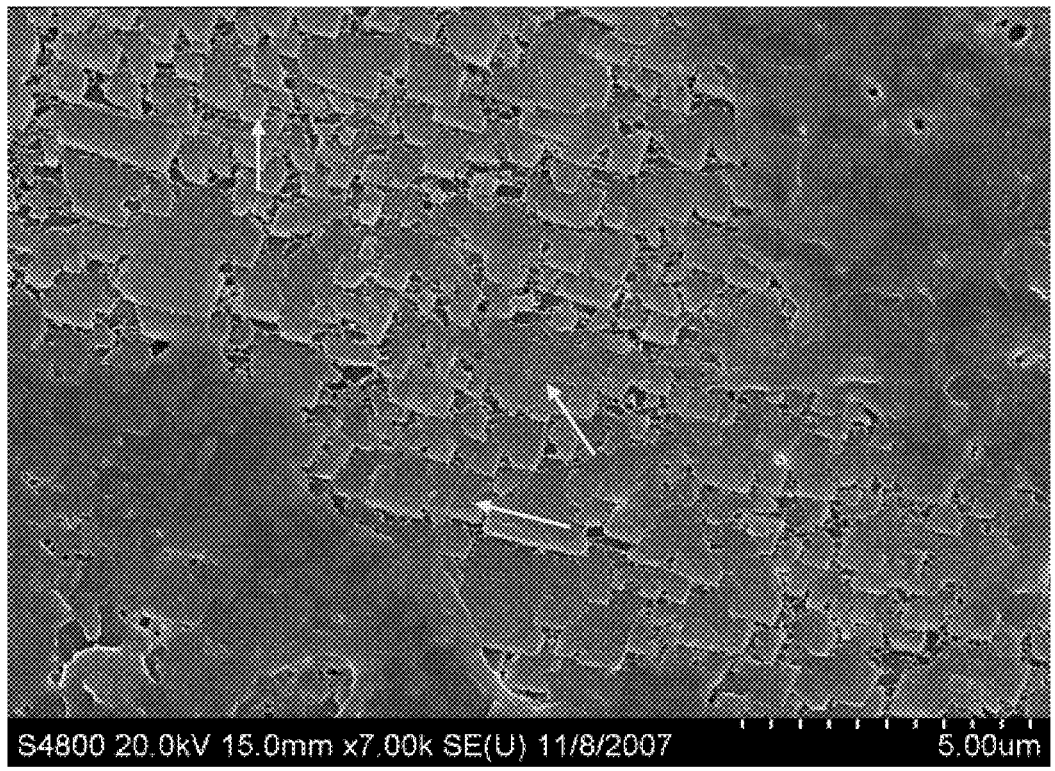
FIG. 3E depicts the area in the rectangle showing developing folia laths and the plasma membrane of hemocytes are associated with the surface. Dendritic processes are indicated with yellow arrows.
Figure 3F:
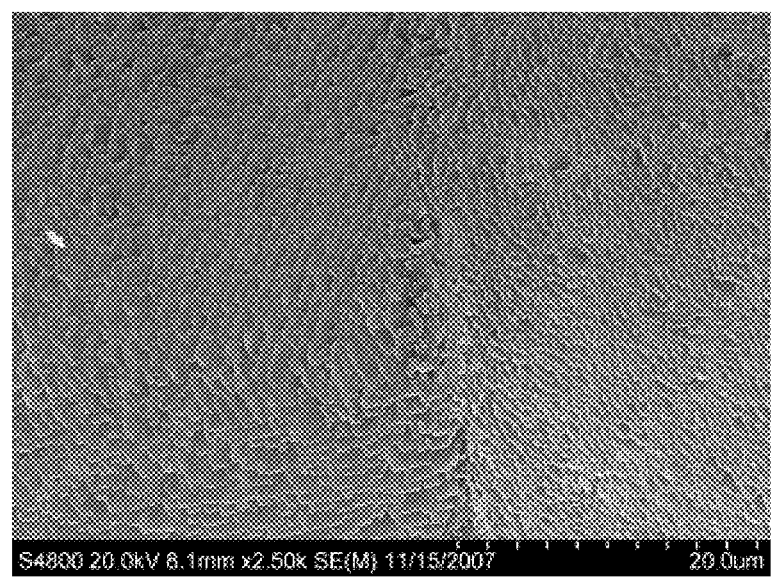
FIG. 3F depicts the point of convergence of two folia pancakes from a confluent folia region.
Figure 3G:
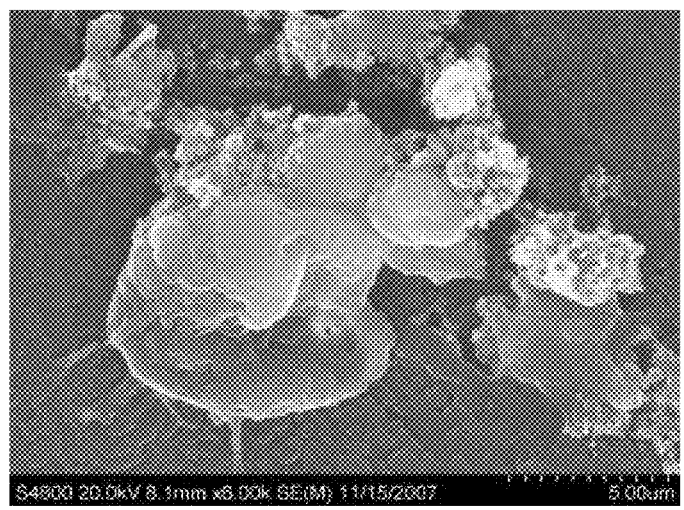
FIGS. 3G to 3J depict evidence of hemocyte activity on the developing folia surface. Hemocytes are present on the surface of developing folia.
Figure 3H:
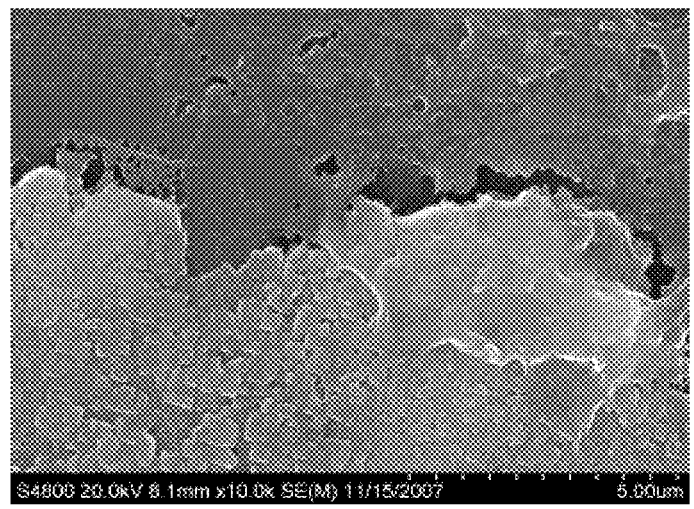
Figure 3I:
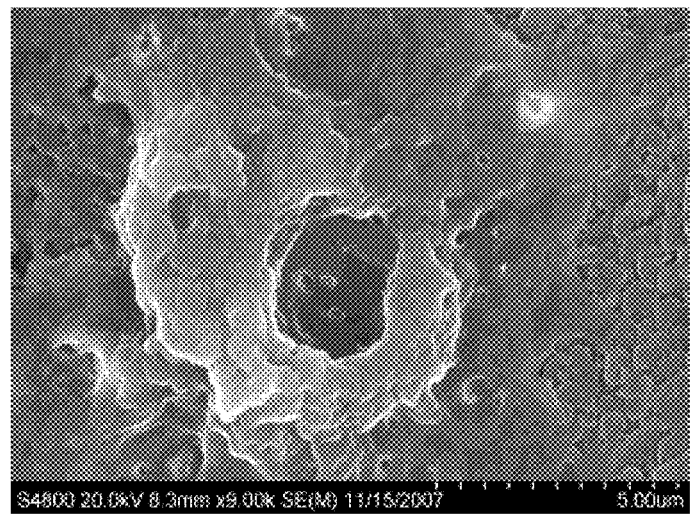
Figure 3J:
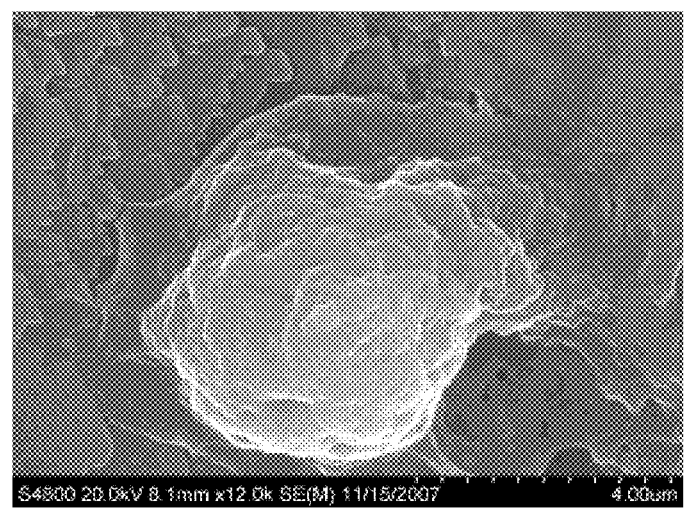
Figure 3K:
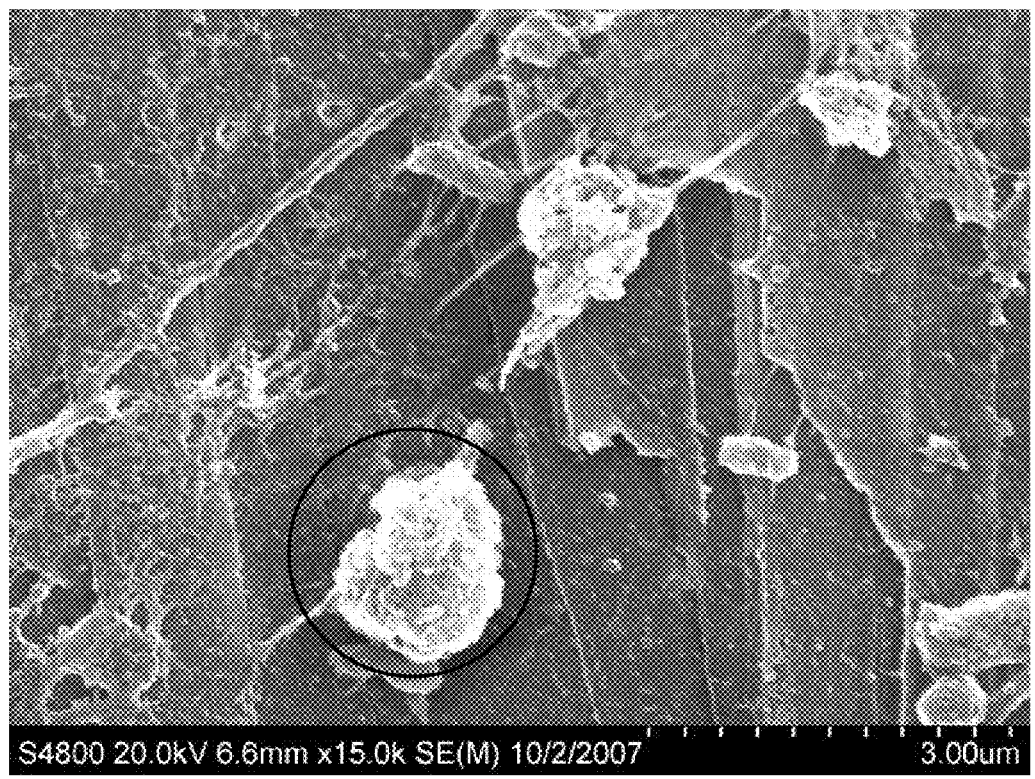
FIG. 3K depicts a crystal laden particle that is visible on the surface of folia laths. The particle is membrane bound and interacts with the crystal surface through dendritic-like processes
Figure 3L:
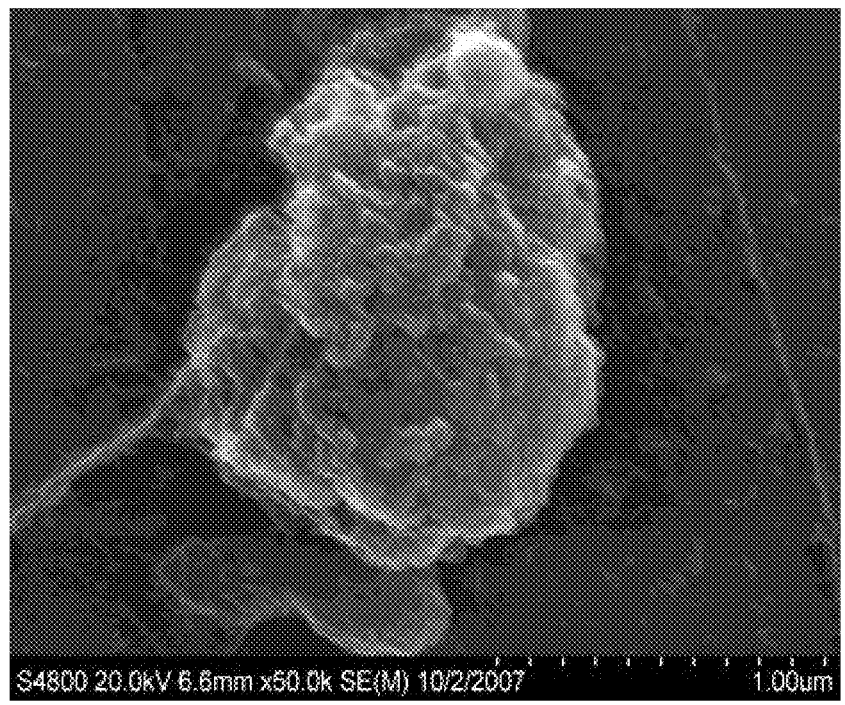
FIG. 3L depicts an enlargement of the crystal in the black circle.
Figure 4D:
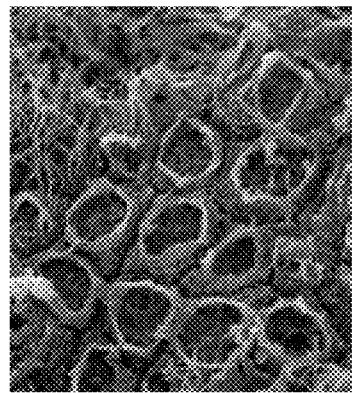
Figure 4E:
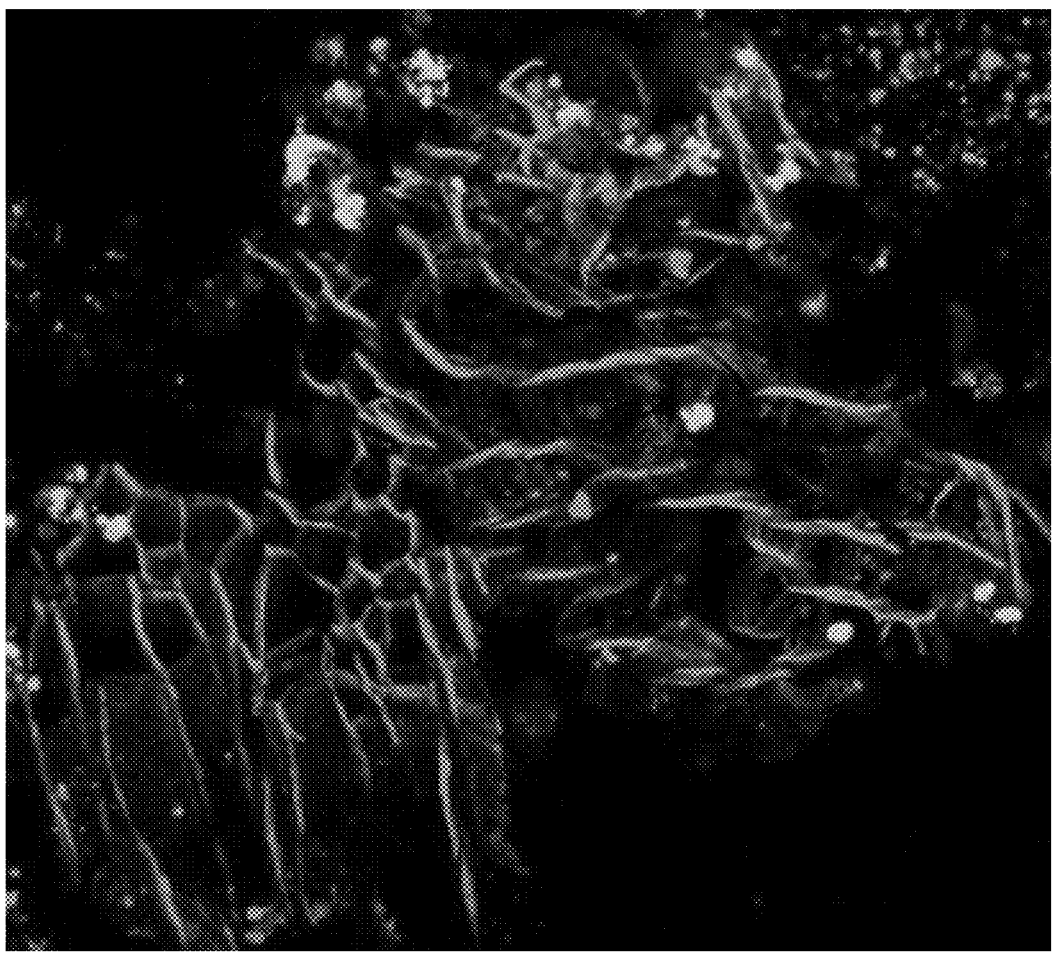

Disclosed herein are methods for deposition of nanocrystalline calcite plates by specialized cells. The methods provide for deposition of nanocrystalline calcite in a controlable manner on a surface of any geometry or on regular or irregular surfaces, inter alia, polished metal surfaces, raw metal surfaces, smooth or irregular organic layers, and the like. The biocompatible surfaces disclosed herein are also referred to a bioceramic coatings having an organized lamella at the nano and/or micro scale. The disclosed process allows the formulator to determine the thickness of the biocompatible surface and the composition thereof. For example, in one iteration a calcite forming hemocyte as disclosed herein can be removed and replaced by a compatible aragonite forming hemocyte, or any iterations thereof.

For the purposes of the present disclosure the terms "method" and "process" are used interchangeably and refer to a collection of one or more steps taken in achieving the results disclosed herein. The results can be formation of a layer or formation of an article comprising the disclosed nanocrystalline calcite deposits.

It has been surprisingly discovered that contacting calcite or aragonite forming cells with an inert surface provides a process for forming a biocompatible layer on the inert surface. Not wishing to be limited by theory, the cells once deposited become organized and come together in an assembly of nanometer thickness and begin depositing foliated calcite onto the surface. The cells can be those which form calcite or aragonite layers.

In one application relating to the use of the disclosed process for preparing a biocompatible surface on a medical device, because the hemocytes disclosed herein can form a biocompatible layer, the cells themselves can be left on the medical device, for example, left in contact with an artificial hip joint thereby affording a more biocompatible layer for contacting the tissue that receives the medical device.

Disclosed are methods wherein oyster blood cells (hemocytes) are manipulated to deposit nacre, a natural calcium carbonate ceramic material used for shell and pearl formation on surfaces not naturally associated with oyster shell formation. Thus, provided is a method for controllably depositing a ceramic film such that the thickness and location of the ceramic film on a surface can be controlled. The disclosed methods have the advantage of providing a calcite layer onto materials that require strong but lightweight protection. The disclosed methods and compositions produced thereby, are based on the harnessing of natural process to generate impact-resistant, corrosion-inhibitive coatings for aircraft, ship hulls and other structures requiring a durable protective finish. In addition, articles comprising the calcite can be formed. For example, synthetic pearls can be fabricated by the disclosed process in a manner more controllable and without risk of death or injury to the pearl-forming species during incubation or seeding.

Oyster shell is a multilayered composite primarily composed of calcite and approximately 1% PMC. Two primary layers of shell microstructures are formed. A thin prismatiic layer (~100 mm in thickness) forms the outer shell layer and is comprised of adjacently positioned columnare polyycrystalline prisms enveloped in PMC. The prisms are oriented such that the long axis is perpendicular to the shell. An inner foliated layer forms 90% of shell mass and is comprised of PMC and flattened, regularly shaped crystal units oriented with their long axes parallel to the plane of the shell which coalesce to form sheets or lamina. Both layers are initiated with the delivery of calcite nonocrystals of intracellular origin to the site of shell formation (mineralization front) by refractive (REF) hemocytes. The first event necessary for biomineralization is to provide a stable substrate upon which cells can adhere. The oyster accomplishes this task by the secretion of an organic periostracal membrane from specialized epithelial cells located in the mantle organ of the mollusk. As such, control of this process affords methods for forming a nanocrystalline calcite layer.

The cells responsible for nanocrystalline calcite deposition can be isolated REF cells or they can be oyster hemocytes (e.g., from withdrawn hemolymph) that include a population of REF cells. The mantle tissue of oysters can also be used to deposit calcite on surfaces where it does not naturally occur or does not occur at the same depth or crystal arrangement. The mantle can be in vivo or it can be isolated as pieces of mantle tissue. The oysters can be Eastern Oyster (*Crassostrea virginica*), European Flat Oyster (*Ostrea edulis*), Kumomoto Oyster (*Crassostrea sikamea*), Olympia Oyster (*Ostrea conchaphila*), Pacific Oyster (*Crassostrea gigas*), or other oysters. Furthermore, because other mollusks, e.g., mussels and clams, also produce calcite, a method of using hemocytes or mantle tissue from mussels and clams is also provided.

In one embodiment, the surface to be coated can be a metal, for example, stainless steel and alloys of aluminum, and titanium. The metal can be in the form of a rod, a foil or a sheet. The metal can be polished. Specific examples include the following: serial sectioned metal rods of: Ti-6V-4Al; 316L stainless steel; Aluminum alloys 2024 and 7075 each polished to a 1 micron finish; polished metal foils of Ti-6V-4Al; 316L stainless steel; and Aluminum alloys 2024 and 7075.

In another embodiment, the surface can be metal vapor deposited on glass (e.g., a cover glass). The metal vapor can be of either Titanium or Aluminum. The cover glass can be 0.17 mm thickness (1.5 grade).

A polycrystalline layer is produced on these surfaces. A polycrystalline layer comprises many nano and micron sized calcite crystals stuck together. Nanocrystals are nanometer sized crystals produced by REF cells. This layer resembles molluscan prismatic shell. It is expected that this method of crystalline deposition will work for other alloys. This cellular biomineralization deposition process is controlled by stimulation of cells to deposit crystals (induction), the degree of surface roughness of the metallic surface and the conjugation of specific peptide sequences which promote cell adhesion, chemotaxis and apoptosis onto the metallic surface of the alloy prior to the addition of cells. This is the first demonstration of a novel crystalline material that is produced by animal cells (e.g. oyster crytoblasts) that can be produced in a highly controlled process.

Refractive granulocytes (hereinafter "REF cells") are circulating immune cells that are found in oyster hemolymph. The cells contain granules, some of which are brillantly bifringent when viewed in polarized light or under differential interference contrast in a light microscope, hence the term "refractive." These cells are approximately 15-20 microns in length, and readily adhere to smooth surfaces. Adherent cells are highly motile and move readily across substrates. These adhered cells appear very thinly stretched on surfaces, with the exception of the cell body, which bears the nucleus and mineralizing vesicles which can be as high as 10 microns in height. REF cells nucleate calcium carbonate crystals within specialized vesicles and deliver the pre-formed crystals to the mineralization front, which is the site of new shell formation.

Large cellular aggregations are observed on surfaces exposed to REF cells, and within these clumps are polycrystalline calcite assemblies. The present results show that REF cells are sufficient for crystal deposition, though there may be other different and uncharacterized cells that also participate in the formation of the mineralized composite.

For example, insertion of either disks, foils, glass, or vapor deposited glass into the notched region of the oyster resulted in a biomineralization response with involvement of the mantle, which is the shell forming organ of an intact oyster. A separate line of experiments, that is removal of REF cells and placement of cells on either disks, foils, glass or vapor deposited metals we were able to observe ex vivo cellular biomineralization without the participation of the mantle.

The ex vivo experiments revealed that REF cells will adhere, move across, form aggregations and deposit crystals and assemble polycrystalline assemblies on every material tested. The REF cells are fully competent to mineralize polycrystalline calcite layers on all tested substrates. In terms of flat pearl production, cellular (ex vivo) biomineralization is new. The fact that calcite is deposited by cells in the absence of the animal's mantle is also novel.

Alternatively, incubated inserts revealed a complexity of membranous layers and the presence of fully formed foliate or prismatic layers which appeared identical to natural or native shell layers. A foliated layer is made up of many individual crystal laths to form a uniform layer. In oyster shell, this layer forms 99% of the shell mass. A prismatic layer comprises polycrystalline calcite assemblies that are bounded by an organic membrane. In oyster shell, this is the first layer that is laid down prior to overgrowth by the foliated layer. A flat pearl is produced when foreign material is introduced between the tissue and the innermost shell of the oyster. This is the way that nacreous buttons were made in colonial times. Flat pearls can have both prismatic and foliated layers on their surfaces.

The cellular mineralization pattern with mantle involvement (insert experiments) revealed the presence of small exosome-like vesicles, some of which contain crystals and others did not. It appeared that some sort of (but yet undescribed) cellular signal transduction mechansim is at work, which causes cells (REF cells) to release crystal bearing exosomes which adhere to the surface of the membrane. From these exosomes crystals emerge and form pancake-like structures which then grow out to form a uniform foliated layer of calcite. Other non-crystalline exosomes are thought to stick to the substrate thus ultimately forming membranous layer, which may act to organize subsquent cellular biomineralization events.

Since the nanocrystalline layer process is cellular; and since one of the participant cell types is known (REF cells), provided is a technology whereby cells can be programmed to produce a particular type of crystal (calcite, aragonite, hematite, hydroxyapatite, or whatever is desired); of a particular dimenson (nanometer or micrometer); of a particular polycrystalline assembly (foliated, prismatic or other) that can be adherent or non-adherent to the underlying substrate.

Implant Coatings and Tissue Engineering

The polycrystalline layer and its process for preparation are applicable for producing novel biomaterials for organ and tissue regeneration, as biocompatible implants for tissue repair, bone and joint implants. The implant application is facilitated by the ability of REF cells (in situ and ex vivo) to produce flat pearl. Furthermore, a single layer, either foliated or prismatic layer or a flat pearl with both layers can be produced.

The present oyster shell-derived biological ceramics are also well tolerated by the human body. Oyster nacre is shown not to elicit an immune response, making it ideal for use in biocompatible medical devices. Metal implants, such as those used in bone repair and artificial joints, are at risk for immediate rejection or failure over time—as are heart valves, which calcify, and heart stents, which eventually clog as a result of immune response. Coating these medical devices with the present calcite finish will allow them to integrate well into the surrounding tissue. For a bone implant, bone morphogenetic protein can be added to the calcite layer.

Tissue engineering applies biological, medical and technical science for the sake of regeneration, maintenance and improvement of tissue functions. Studies concerning new materials for cell culture scaffolds are a quickly developing domain of biomedical engineering. See Jaegermann et al., Calcite-based material for tissue engineering ceramic scaffolds, Presentation: Oral at E-MRS Fall Meeting 2008, Symposium L. The present method of depositing calcite provides a novel scaffold for human bone growth and even tissue and organ regeneration. Furthermore, the present method provides coatings for scaffold for human bone growth and even tissue and organ regeneration. The scaffolds and related structurs produced by the disclosed method are also provided.

Antifouling

The polycrystalline layer and its process for preparation are applicable to environmentally benign antifouling methods, cellular adhesives and protective coatings. The shipbuilding industry has directed much effort toward ways of limiting escalating coating costs. Of special concern with respect to increasing coating costs are segregated seawater ballast tanks. The use of a calcite-type coating instead of a traditional organic-type maintenance coating represents a possible alternative approach for controlling corrosion in the segregated tanks with a substantial savings in cost. As a result, National Steel and Shipbuilding Company acting on behalf of the Maritime Administration under the National Shipbuilding Research Program authorized the Ocean City Research Corporation to undertake a laboratory study which continued previous investigations of the feasibility of applying calcite-type coatings to segregated ballast tanks. The testing was intended to demonstrate and quantify the long-term corrosion protection afforded by the calcite coatings. The laboratory tests demonstrated that well developed calcite films can reduce the corrosion rate of steel in a seawater ballast tank. Furthermore, calcite films can reduce the cathodic protection current demand required for corrosion control by a factor of five. For more information, see Corrosion Protection by Calcite-Type Coatings, Jr Gehring George A.; OCEAN CITY RESEARCH CORP NJ, Storming Media, Pentagon Reports; fast, definitive and complete; Report Date: OCT 1989; Report Number: A565254; www.stormingmedia.us. Thus, provided are methods of preventing fouling and corrosion of ballast tanks. Coated ballast tanks produced by this method are also provided. Additionally, provided is method of generating a calcite or other layer on an object to provide a protective barrier, such as an anticorrison barrier for an artifact in the marine environment. This would be a thick multi-layer coating. Products produced by this method are also provided.

In the antifouling context, the nanocrystalline calcite coating produced can include other antifouling molecules, or cellular signaling molecules that would prevent attachment of settlement of bacteria and other macrofouling organisms. The antifouling method, can include the depositon of multiple layers of calcite interleafed with organic membranes with appropriate signaling molecules included. In another embodiment, the crystals can be be toxic to the targeted fouling community. Products produced by this method are also provided.

The present methods can be useful in promoting the attachment and settlement of organisms and bacteria by coating an object with nanocrystalline calcite that would promote the attachment and settlement of organisms and bacteria. In one embodiment, this would be useful in aquaculture settings where larval organisms are grown out as adults for human food consumption. In this embodiment, this process would produce a thin nanocrystalline layer associated with a thicker signal rich membrane. Products produced by this method are also provided.

The present methods can be useful to provide benign or biocompatible coatings, for example, as a specified coating on an implant for human medicine; such as for hip or pins or any other surface or organ that has to be biocompatibile to prevent host rejection. In this instance the calcite layer is likely to be thin, so it can be eventually incorporated into the host. Products produced by this method are also provided.

Alternatively, the present method can be used to promote a host response, such as encapsulation. In this scenario, the coating is benign and remains permanently isolated within the organism or patient. This would be a multi-layer coating. Products produced by this method are also provided. An example of a product produced by this method would be a radio-frequency identification (RFID) device or other device. A further example would be the production of a cultured pearl.

The cellular production of novel crystalline surfaces is ideal for improved pearl seeding in the pearl culture industry. The currently accepted procedure for pearl culture is to embed a small round seed from the nacreous layer of a freshwater mussel within an incision in the viseral mass of *Pinctada* spp, (the pearl oyster). In addition to the seed pearl; a small piece of foreign mantle tissue is also inserted. If the animal is not killed in the process, many months later a pearl is harvested. The entire pearl formation process is immune system driven, so the ideal pearl seeds can be developed, which include a nanocrystalline calcite coating and the signaling molecules (or bacterial peptides such as fMLF) which would induce a vigorous immune response in the host animal as outlined in the immunoreactive example above. Thus, a calcite seed can be used to stimulate innate cellular immunity to produce more calcite. This is a special case of immunoreactive inducible nanocrystalline surfaces.

The cellular (ex vivo) technology disclosed herein can be housed in a bioreactor to produce scalable quantities of materials from milligram to kilogram amounts. Thus, present methods and compositions can also be a source materials for other applications—such as nanophase bulk materials from a bioreactor.

A method for deposition of nanocrystalline calcite plates by specialized epithelial tissue (oyster mantle) onto metallic surfaces is presented. Tested surfaces include stainless steel and alloys of aluminum, and titanium upon which a polycrystalline layer is produced. This layer resembles molluscan prismatic shell. It is likely that this method of crystalline deposition will work for other alloys. This epithelial biomineralization deposition process is controlled by stimulation of cells to deposit crystals (induction), the degree of surface roughness of the metallic surface and the conjugation of specific peptide sequences which promote cell adhesion, chemotaxis and apoptosis onto the metallic surface of the alloy prior to the addition of cells.

The present method for depositing nanocrystalline calcite can further include the step of contacting the surface to be coated with a stimulatory peptide. The specific peptides that are effective in this method can be readily determined using the assays described herein. In a specific embodiment, the peptide can comprise X-G-D, where X is lysine or arginine, for example, a peptide comprising or consisting of K-G-D or a peptide comprising or consisting of R-G-D. In a further embodiment, the peptide can be fM-L-F and peptides with similar amino acids. When immobilized to the surface being coated, the stimulatory peptide causes the epithelia (in vivo) or isolated REF cells to preferentially deposit crystals upon the surface in the region where the peptides are localized. By the same token, areas of a surface can be coated with peptide inhibitors of cellular adhesion to prevent deposition of calcite in those areas. By the use of peptide stimulators or peptide inhibitors, or both, the pattern of calcite deposition (e.g., location and thickness) can be finely controlled.

The peptides can be chemically conjugated to the surface or otherwise immobilized on the surface. The immobilization is only required for long enough to stimulate crystal formation by the cells. Standard conjugation chemistry can be used to link the peptides to the surface.

It is recognized that there are oyster hemocyte-produced homologues to human immune-modulators, such as a mammalian-like transforming growth factor-$\beta$ (TGF-$\beta$) receptor, I$\kappa$B kinase (IKK) protein), TNF-$\alpha$, and IL-17 and toll receptors. There are also pro- and anti-inflammatory cytokines: TNF-$\alpha$, TGF-$\beta$, IL-4, IL-10, and IL-12. Alpha and beta adrenegenic receptors, and every part of the apoptotic cascade also appear to be present in oysters. The activity of these molecules can be increased or decreased in the environment of the REF cells (in situ or ex vivo) to modulate the calcite producing-activity of the REF cells. The increase or decrease of activity can be the result of an increase or decrease in amount of the molecules, or modification of the molecules to reduce or enhance their function. Thus, provided is a method of controlling the deposition of nanocrystalline calcite by REF cells in vivo or ex vivo by modulating the activity of an immune modulator, cell signal receptor/ligand or apoptotic pathway molecule. Freund's adjuvant or other adjuvant can be used for immune stimulation to enhance crystal formation or encapsulation.

A calcite coated object made according to the processes of the invention is also provided. The calcite coated object is not found with a calcite coating in nature. Alternatively, the coated object is found with a calcite coating in nature, but the coating is of a different nanocrystalline array or has a different thickness of nanocrystalline layers compared to the same object found in nature. Examples of the calcite coated objects of the invention include marine surfaces (e.g., ships hulls, ballast tanks, etc), aircraft surfaces (e.g., fuselage, etc.), medical/dental implants (e.g., bone/organ scaffolds).

Disclosed herein is a process for forming a microcrystalline calcite layer comprising:
 a) contacting a surface with an isolated mollusk cell; and
 b) forming a nanocrystalline calcite deposit on the surface.

In another embodiment, the process comprises:
 a) contacting a surface with oyster mantle; and
 b) forming a nanocrystalline calcite deposit on the surface.

In one iteration of this embodiment, the disclosed process relates to forming a synthetic pearl, comprising:
 a) contacting a suitable solid with oyster mantle; and
 b) forming a synthetic pearl comprising layered nanocrystalline calcite.

In another embodiment, the disclosed process relates to forming a biocompatible layer on an inert surface, comprising;
 a) contacting an inert surface with an isolated mollusk cell; and
 b) forming a biocompatible layer on the inert surface.

As it relates to this embodiment, a biocompatible nanocrystalline layer of calcite can be formed on bio-implant device, for example, on a titanium alloy or stainless steel implant. A bio-implant is defined herein as a non-living tissue device surgically implanted in a person's body to replace damaged tissue. Common areas of application include orthopedic (especially maxillofacial) re-constructive prosthesis, cardiac prostheses (artificial heart valves like the Chitra heart valve. In addition, shunts implanted to drain fluids from one section of the body to another can be coated with the biocompatible layers disclosed herein by the disclosed process.

The disclosed process further relates to forming a biocompatible surface on an inert surface, comprising:
 a) contacting an inert surface with a source of refractive hemocytes;
 b) exposing the inert surface in contact with the refractive hemocytes to viable oyster mantle; and
 c) forming a biocompatible nanocrystalline calcite layer on the inert surface wherein formation of the calcite layer is induced by stimulating an immune response thereby increasing the number of refractive hemocytes.

The disclosed process yet further relates to forming a biocompatible surface on an inert surface, comprising:
 a) contacting an inert surface with a mollusk shell;
 b) stimulating an immune response by manipulating the surface of the shell in the presence of refractive hemocytes; and
 c) forming a biocompatible nanocrystalline calcite layer on the inert surface.

EXAMPLE 1

In Vivo Calcite Deposition on Non-Native Surface

Materials and Methods
Oyster Collection and Holding

Eastern oysters, *Crassostrea virginica* were obtained from Pemaquid Oyster Company Inc. (P.O. Box 302, Waldoboro, Me. 04572). After receiving, the oysters were held in a 180 gallon (681 liter) tank at 18° C. in artificial sea water at 31% salinity with saturating levels of dissolved oxygen. The animals were fed twice a week with Shellfish Diet 1800® (Reed Mariculture Inc., 520 McGlincy Lane #1, Campbell, Calif. 95008). Tank water was continuously filtered except for several hours during feeding. Experimental animals were kept in 50 gallon holding tanks under the same conditions as the acclimation tank.

Preparation of Metal Alloy Disks and Foils for Implantation

Polished (1 µm finish) titanium ($Ti_6Al_4V$) and aluminum (AA2024, AA7075) and 316-L stainless steel disks measuring approximately 1 cm in diameter by 1 mm thick were cleaned by a series of 5 minute washes, first in acetone followed by isopropyl alcohol and ending with methanol. The disks were flash dried on a heat block prior to implantation into the oyster. Alternatively, polished metal alloy foils (titanium, $Ti_6Al_4V$; aluminum alloys AA2024, AA7075 and 316L stainless steel) were also tested. Each foil square measured 1 $cm^2$ by XXX mm thick. Foil inserts were cleaned and prepared in the same manner as the metal disks.

Implantation Procedures

Implantation was accomplished by removing just enough of the shell margin or edge with a diamond saw so that the disks could be inserted into the extrapallial cavity (which is the region between the mantle tissue and the shell) just inside the most active margin of shell formation. In some cases, the disks were placed deep enough into the extrapallial cavity to come in contact with the with the adductor region of the mantle. The adductor is the muscle responsible for maintaining valve closure. Implants remained in contact with the shell facing side of the mantle organ throughout the duration of their time of incubation. Implants were collected at 8 day, 14 day and 28 day intervals. Square foils were placed into a "V" shaped notch was cut into the shell margin using a tile saw with a diamond blade and the foils were glued in place using an ethyl cyanoacrylate based adhesive. Incubations extended up to 14 days. These implants were excised from the shell with a scalpel prior to analysis.

Fixation, Imaging and X-Ray Microprobe (EDS) Analysis

Immediately following removal, implants were viewed on a Nikon AZ-100 microscope using both FITC and epi-polarization channels at low magnification to verify the presence of a mineralized coating. After imaging, the samples were washed for 5 min in 0.2 µm filtered seawater. The samples were fixed for one hour in 4% paraformaldehyde 0.1M sodium cacodylate trihydrate buffer at pH 8. Following fixation, samples were washed 3× in 0.005M sodium cacodylate trihydrate buffer, pH 8.0 followed by dehydration through a series of ethanol washes starting with 25% ethanol in water, followed by 50, 75, 90 and 100% ethanol for 10 min each. After dehydration, the samples were critically point dried and sputter coated with platinum (then visualized using a field emission 4800S Hitachi high resolution scanning electron microscope equipped with an Oxford INCA Energy 200 EDS and a GW Electronics Centaurus backscatter detector.

Fixation and Imaging of Oyster Mantle Sections

To obtain mantle tissue sections, live oysters were relaxed by injection of a 1% cocaine solution (dissolved in molluscan PBS) into the adductor muscle. Within 5 minutes the shells would gape, and the animal would be transferred to a cold solution of 10% paraformaldehyde in 0.1M sodium cacodylate trihydrate buffer at pH 8. The animal was fixed overnight at 4° C., the animal's hinge ligament was manually opened and the flat valve was excised from the adductor muscle.

Fixed relaxed mantle sections were dissected near the growing margin of shell. These sections were washed 3× in 0.005M sodium cacodylate trihydrate buffer, pH 8.0 followed by dehydration through a series of ethanol washes starting with 25% ethanol in water, followed by 50, 75, 90 and 100% ethanol for 10 min each. After dehydration, the tissue sections were critically point dried and sputter coated with platinum then visualized using a JEOL 5300 LV scanning electron microscope.

Imaging of Live Prismatic Shell Formation by Epi-Fluorescent and Laser Scanning Microscopy Notched adult oysters were held overnight in 50 gallon holding tanks. Using a 1.5" 21 gauge sterile needle affixed to a 3 ml sterile plastic syringe, approximately 1 mL of hemolymph was removed from the adductor muscle of the intact animal and transferred to a 1.5 ml plastic microfuge tube. To fluorescently vital label living hemocytes, 10 µL of calcein AM ester (Invitrogen) was added to the tube and incubated for 1-2 hours at room temperature. The tube bearing the cells was centrifuged at 3,000 g (RCF at Tip) for 3 minutes and the supernatant was discarded. The cell pellet was gently re-suspended and washed in mollusan phosphate buffered saline (molluscan PBS recipe: 20 mM sodium phosphate, 150 mM or higher NaCl, the exact concentration of sodium chloride is dependent upon the osmolality of the oyster's holding tank, pH 7.4). The washed and labeled cell suspension was re-injected into the subject oyster's adductor muscle and the animal was replaced into the aquarium. After about a 1-2 hour incubation, the oyster was relaxed by injection of 1% cocaine solution (dissolved in molluscan PBS) into the adductor muscle. Within 5 minutes the shells would gape, and the animal's hinge ligament was manually opened and the flat valve was excised from the adductor muscle. Live relaxed mantle sections were dissected near the growing margin of shell. To visualize live hemocytes on the growing prismatic layer margin, the shell facing side of the mantle was affixed to a glass cover slip and mounted to a glass slide. These slides were visualized on a Zeiss LSM-510 microscope using the Zeiss Plan Neofluar 40× oil 1.3 N.A. objective. Confocal stacks using both FITC and TRITC wide field channels were recorded and three dimensional projections obtained using the Zeiss microscope's software. Two channel images (FITC and DIC) of intact prismatic shell pieces were obtained from a Zeiss Axiovert 135 fluorescent microscope using a Zeiss Plan Neofluar 40× oil 1.3 N.A. objective and a Zeiss Axiocam MRc5 digital camera system.

Figure 6:
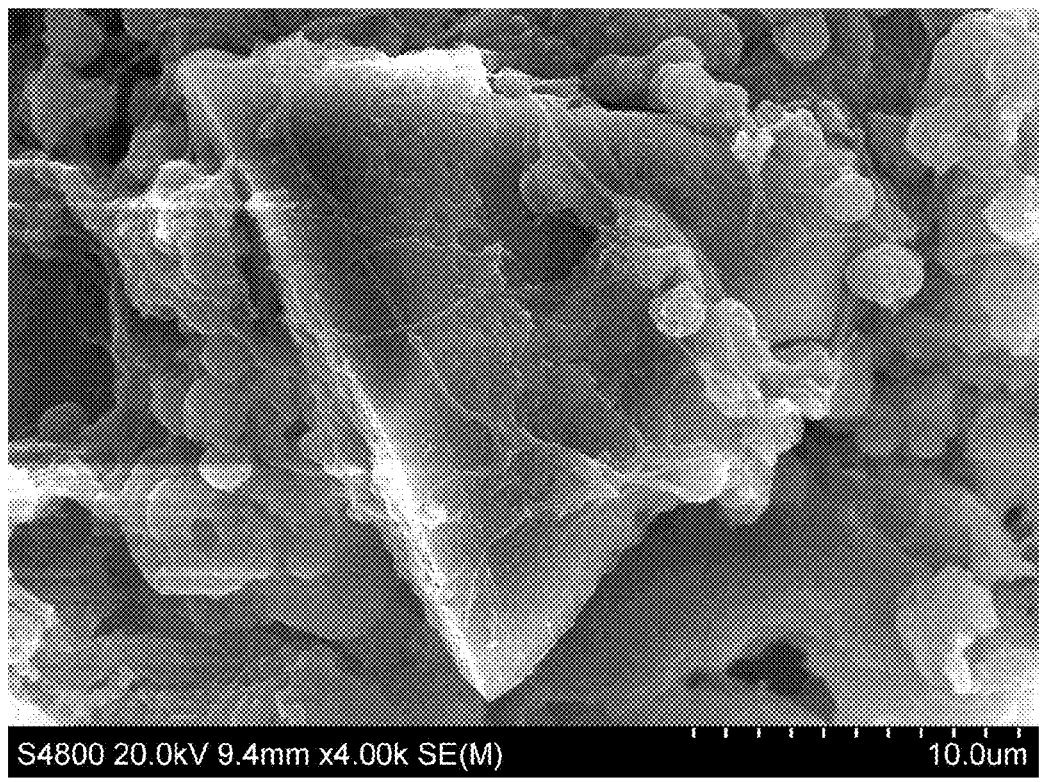
FIG. 6 depicts the polycrystalline assembly on $Ti_6Al_4V$.

FIG. 6 depicts the polycrystalline assembly on $Ti_6Al_4V$.

EXAMPLE 2

Oyster Hemocyte Cell Culture Protocol

Preparation:

Molluscan L15 culture medium: Sterile L15 Medium Leibovitz, Sigma (catalog number L1518) to which sodium chloride was added to match cell osmolality. The media was supplemented with penicillin (10 units/mL) and streptomycin (250 µg/mL) final concentration.

The cover glass or metal insert was washed serially (5 minute duration each wash) in acetone, followed by isopropanol then methanol and ethanol, with a final sterile water rinse. The substrates were taken to dryness on a slide warmer set at 45° C.

Procedure:

Approximately 100 µl of hemocytes were withdrawn using a sterile needle and syringe from the oyster's adductor muscle and incubated for 90-120 minutes on glass or metal substrates. The cells were rinsed with 0.22 µm filtered sterile seawater which matched cell osmolality. The washed surfaces were placed into a cell culture 12 well plate (Corning Incorporated; Costar catalog number 3512) followed by the addition of the molluscan L15 culture medium. The plates were incubated at 20° C. and the media was replaced daily. All manipulations were conducted in a laminar flow hood under sterile conditions.

Figure 5:
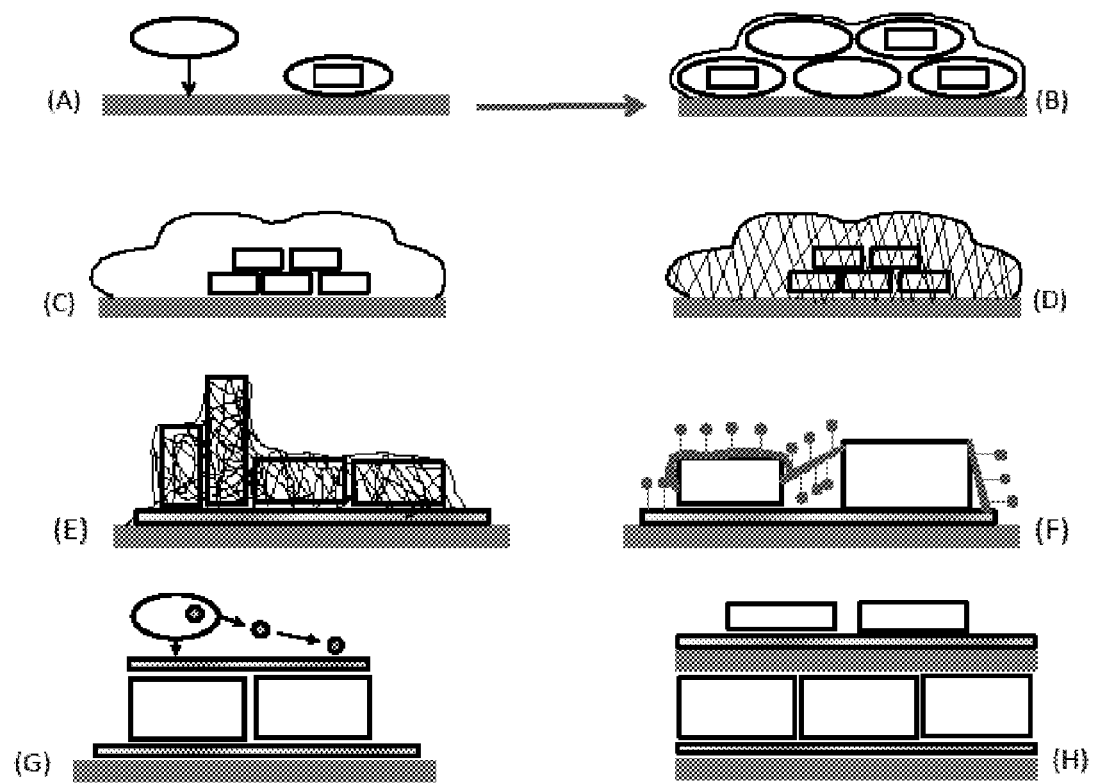
FIG. 5 is a diagram of the process of calcite deposition by isolated REF cells as described in Example 2.

Results:

Layers of calcite were deposited by the isolated REF cells as shown in FIG. 5. In FIG. 5*a*, cells adhere to a substrate then aggregate to form a syncytium as depicted in FIG. 5*b*. The syncytium forms a polycrystalline assembly (FIG. 5*c*) which then forms a coating over the crystal assembly consisting of apoptotic syncytium plasma membranes, proteins and other debris as depicted in FIG. 5*d*. FIG. 5*e* depicts how crystals then grow out of the syncytium debris. In FIG. 5*f*, peptides, proteins and lipid signals are depicted on crystals that induce cells to release their exosomes. The exosomes (FIG. 5*g*) add additional crystals and membranes to form a new mineralized membrane. FIG. 5*h* shows the shell layer formation after the steps in FIG. 5*a* to FIG. 5*g* are iteratively repeated.

The present process provides a biocompatible layer that can comprise a mineralized component and a matrix component. As the cells coalesce into an assembly and begin forming the crystal assembly, the apoptotic syncytium plasma membranes will comprise cellular debris that will form the matrix component that can surround the mineralized, calcite or aragonite, component. The thickness of the resulting nanolayer will therefore be uniform such that subsequently formed layers will also have a uniformly thickness.

The inert surfaces that can have a biocompatible layer formed thereon can comprise any material having a uniform surface, for example, metal, glass, and the like. In one embodiment, the surfaces are polished to a mirror finish.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A process of depositing nanocrystalline calcite on a solid surface, comprising
   contacting the solid surface with an isolated mollusk cell, the isolated mollusk cell having been withdrawn and removed from the body of a mollusk and located on the solid surface; and
   culturing the isolated mollusk cell on the solid surface, the isolated mollusk cell depositing nanocrystalline calcite on the solid surface as the isolated mollusk cell is cultured on the solid surface.

2. The process according to claim 1, wherein the solid surface comprises a metal.

3. The process according to claim 2, wherein the metal is titanium or aluminum.

4. The process according to claim 2, wherein the solid surface comprising the metal has a mirror finish.

5. The process according to claim 2, wherein the metal is aluminum and the aluminum is a component of an aluminum alloy.

6. The process according to claim 2, wherein the metal is a component of a stainless steel.

7. The process according to claim 1, wherein the isolated mollusk cell is a mollusk mantle epithelial cell.

8. The process according to claim 1, wherein the isolated mollusk cell is a mollusk hemocyte.

9. The process according to claim 8, wherein the mollusk hemocyte is refractive granulocyte.

10. The process according to claim 1, further comprising the step of contacting or immobilizing on the solid surface a peptide selected from the group consisting of X-G-D, where X is lysine or arginine, and fM-L-F.

11. The process according to claim 10, wherein the peptide is conjugated to the solid surface.

12. The process according to claim 1, wherein the isolated mollusk cell is an oyster cell, a mussel cell or a clam cell.

13. A process of depositing nanocrystalline calcite on a solid surface, comprising:
- contacting a mollusk mantle with the solid surface, the solid surface comprising a metal; and
- culturing the mollusk mantel on the solid surface, the mollusk mantle depositing nanocrystalline calcite on the solid surface as the mollusk mantle is cultured.

14. The process according to claim 13, wherein the solid surface comprising the metal has a mirror finish.

15. The process according to claim 13, wherein the metal is titanium or aluminum.

16. The process according to claim 13, further comprising the step of contacting or immobilizing on the solid surface a peptide selected from the group consisting of X-G-D, where X is lysine or arginine, and fM-L-F.

17. The process according to claim 16, wherein the peptide is conjugated to the solid surface.

18. The process according to claim 13, wherein the mollusk mantle is an oyster mantle, a mussel mantle or a clam mantle.

19. The process according to claim 13, wherein the metal is a component of a metal alloy.

20. The process according to claim 19, wherein the metal alloy is an aluminum alloy.

21. The process according to claim 19, wherein the metal alloy is a stainless steel.

* * * * *